United States Patent [19]

Gottstein et al.

[11] 4,172,196
[45] Oct. 23, 1979

[54] CERTAIN 7-α-SUBSTITUTED-α-HYDROX-YACETAMIDO-3-(1-CARBOXYMETHYLTET-RAZOL-5-YL-THIOMETHYL)-3-CEPHEM-4-CARBOXYLIC ACIDS

[75] Inventors: William J. Gottstein, Fayetteville; Murray A. Kaplan, Syracuse; Alphonse P. Granatek, Baldwinsville, all of N.Y.

[73] Assignee: Bristol-Myers Company, New York, N.Y.

[21] Appl. No.: 709,478

[22] Filed: Jul. 28, 1976

Related U.S. Application Data

[60] Division of Ser. No. 590,971, Jun. 27, 1975, which is a continuation-in-part of Ser. No. 502,991, Sep. 3, 1974, abandoned.

[51] Int. Cl.$^2$ .............................................. C07D 501/36
[52] U.S. Cl. ........................................ 544/26; 544/27; 424/246
[58] Field of Search .................................. 260/243 C

[56] References Cited

U.S. PATENT DOCUMENTS 3,989,694  11/1976  Berges ............................. 260/243 C

*Primary Examiner*—Nicholas S. Rizzo
*Attorney, Agent, or Firm*—Herbert W. Taylor, Jr.

[57] ABSTRACT

Certain 7-acylamido-3-(1-carboxymethyltetrazol-5-yl-thiomethyl)-3-cephem-4-carboxylic acids and their salts and easily hydrolyzed esters of the 4-carboxyl group were synthesized and found to be potent anti-bacterial agents which exhibited good aqueous solubilty. In a preferred embodiment the 7-substituent was D-α-hydroxyphenylcetamido.

14 Claims, No Drawings

CERTAIN 7-α-SUBSTITUTED-α-HYDROXYACETAMIDO-3-(1-CARBOXYMETHYLTETRAZOL-5-YL-THIOMETHYL)-3-CEPHEM-4-CARBOXYLIC ACIDS

CROSS-REFERENCE TO RELATED APPLICATIONS

This application is a division of our prior, copending application Ser. No. 590,971 filed June 27, 1975 which in turn was a continuation-in-part of prior, copending application Ser. No. 502,991 filed Sept. 3, 1974 and now abandoned.

BACKGROUND OF THE INVENTION (1) Field of the Invention

The cephalosporins of the present invention in general possess the usual attributes of such compounds and are particularly useful in the treatment of bacterial infections.

(2) Description of the Prior Art

The cephalosporins are a well-known group of semi-synthetic antibacterial agents made originally, for example, by acylation of the 7-amino group of the nucelus 7-aminocephalosporanic acid (7-ACA) and later by similar acylation of nuclei derived therefrom, as by modification of its substituent at the 3-position. Various reviews have appeared in the scientific literature (e.g. Cephalosporins and Penicillins—Chemistry and Biology, edited by Edwin H. Flynn, Academic Press, New York, 1972, and particularly pages 554–569) and in the patent literature, e.g. as in U.S. Pat. Nos. 3,687,948; 3,741,965; 3,743,644; 3,759,904; 3,759,905; 3,766,175; 3,766,906; 3,769,281; 3,796,801; 3,799,923; 3,812,116; 3,813,388; 3,814,754 and 3,814,755 (all U.S. Class 260-243C).

Issued disclosures of 3-thiolated cephalosporins in which the 7-substituent is 7-mandelamido (7-α-hydroxyphenylacetamido) are found, for example, in U.S. Pat. No. 3,641,021, France No. 73.10112, U.S. Pat. No. 3,796,801, Great Britain No. 1,328,340 (Farmdoc 38983T), U.S. Pat. No. 3,701,775, Japan No. 4844293 (Farmdoc 55334U) and in Hoover et al., J. Med. Chem. 17(1), 34–41 (1974) and Wick et al., Antimicrobial Ag. Chemo., 1(3), 221-234 (1972).

U.S. Pat. No. 3,819,623 (and, for example, also U.K. No. 1,295,841 and West Germany No. 1,953,861) discloses specifically and with working details the preparation of 2-mercapto-1,3,4-thiadiazole-5-acetic acid and its conversion to 7-(1H-tetrazol-1-ylacetamido)-3-(5-carboxymethyl-1,3,4-thiadiazol-2-ylthiomethyl)-3-cephem-4-carboxylic acid which is also disclosed in West Germany Offenlegungsschrift No. 2,262,262.

SUMMARY OF THE INVENTION

The present invention provides the compounds having the structure:

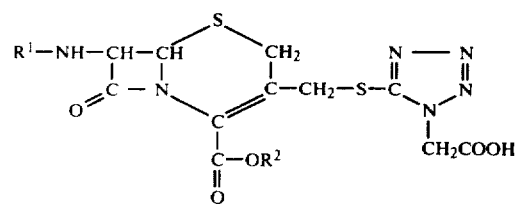

(often written herein as

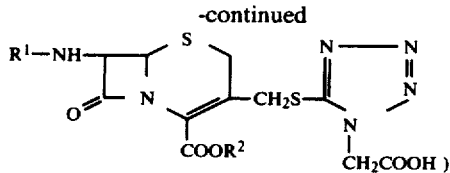

-continued wherein R¹ is acyl as defined below or hydrogen and R² is hydrogen or the group having the formula

wherein, when W represents hydrogen, Z represents (lower)alkanoyl, benzoyl, naphthoyl, furoyl, thenoyl, nitrobenzoyl, methylbenzoyl, halobenzoyl, phenylbenzoyl, N-phthalimido, N-succinimido, N-saccharino, N-(lower)alkylcarbamoyl, (lower)alkoxy, (lower)alkylthio, phenoxy, carbalkoxy, carbobenzoxy, carbamoyl, benzyloxy, chlorobenzyloxy, carbophenoxy, carbo-tert.-butoxy or (lower)alkylsulfonyl, and when W represents carbalkoxy, Z represents carbalkoxy and, when W represents phenyl, Z represents benzoyl or cyano or wherein W and Z taken together represent 2-oxocycloalkyl containing 4 to 8 carbon atoms inclusive. In the preferred embodiments of this invention R² is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl.

As set forth below in more detail the present invention also provides salts of these acids. The stereochemistry of the bicyclic nucleus is that found in Cephalosporin C.

Acyl (R¹) includes, but is not limited to, α-hydroxyphenylacetyl and α-formyloxyphenylacetyl.

Another preferred embodiment of the present invention consists of the compounds of Formula I having the D configuration in the 7-side chain wherein R¹ has the structure

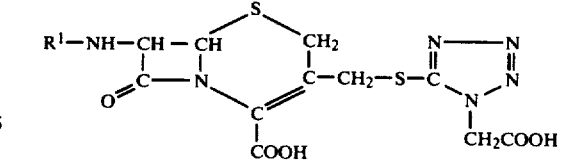

and Y is hydrogen, chlorine, bromine, fluorine, trifluoromethyl, amino, nitro, hydroxy, lower alkyl of 1–4 carbon atoms or lower alkoxy of 1–4 carbon atoms.

Another preferred embodiment of the present invention consists of the compounds having the formula

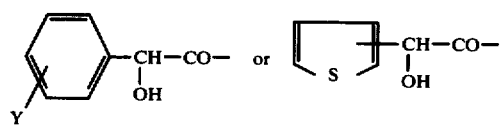

wherein R¹ has the formula

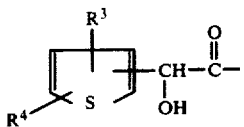

wherein $R^3$ and $R^4$ are each hydrogen, chloro, bromo, fluoro, iodo, nitro, (lower)alkyl, (lower)alkoxy, (lower)alkylthio, di(lower)alkylamino, (lower)alkanoylamino, (lower)alkanoyl or (lower)alkylsulfonyl.

Another preferred embodiment of the present invention consists of the compounds having the formula

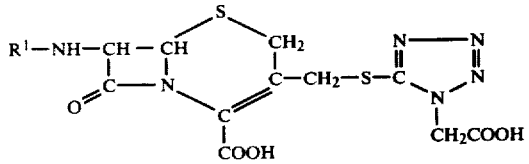

wherein $R^1$ has the formula

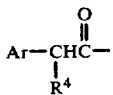

wherein $R^4$ represents hydroxy and (lower)alkanoyloxy; and Ar represents a monovalent radical having one of the formulae

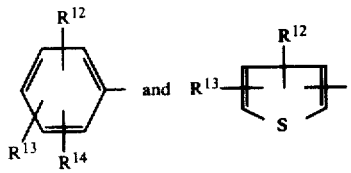

wherein $R^{12}$, $R^{13}$ and $R^{14}$ are each a member selected from the group consisting of hydrogen, chloro, bromo, iodo, trifluoromethyl, (lower)alkyl and (lower)alkoxy.

Such salts include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)alkylpiperidine, e.g. N-ethylpiperidine, and other amines which have been used to form salts with benzylpenicillin.

The present invention also provides the process for the production of the antibacterial agents having the structure

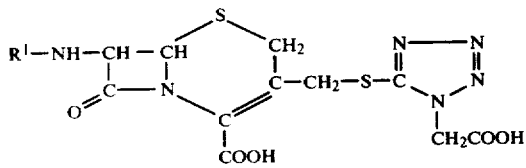

wherein $R^1$ is acyl as defined above which comprises reacting a compound of the formula

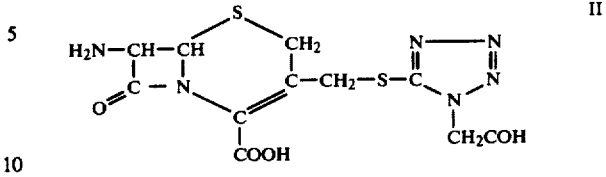

or a salt or easily hydrolyzed ester or Schiff base as with benzaldehyde or salicylaldehyde thereof (including, but not limited to, those of U.S. Pat. No. 3,284,451 and U.K. No. 1,229,453 and any of the silyl esters described in U.S. Pat. No. 3,249,622 for use with 7-aminopenicillanic acid and used in Great Britain No. 1,073,530 and particularly the pivaloyloxymethyl, acetoxymethyl, methoxymethyl, acetonyl, phenacyl, p-nitrobenzyl, $\beta,\beta,\beta$-trichloroethyl, 3-phthalidyl and 5-indanyl esters) thereof with an organic monocarboxylic acid chloride or a functional equivalent thereof as an acylating agent.

Such functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acid such as diphenylacetic acid. A particularly useful anhydride is an N-carboxy-anhydride (also called a Leuch's anhydride; see U.S. Pat. Nos. 3,080,356 and 3,206,455) including but not limited to D-mandelic acid carboxyanhydride (U.S. Pat. No. 3,167,549) or the corresponding substituted D-mandelic acid carboxyanhydride. In addition, an acid azide or an active ester or thioester (e.g. with p-nitrophenyl, 2,4-dinitrophenol, thiophenol, thioacetic acid) may be used or the free acid itself may be coupled with compound II after first reacting said free acid with N,N'-dimethylchloroformiminium chloride [cf. Great Britain No. 1,008,170 and Novak and Weichet, Experientia XXI, 6, 360 (1965)] or by the use of enzymes or of an N,N'-carbonyldiimidazole or an N,N'-carbonylditriazole [cf. South African patent specification No. 63/2684] or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkylylamine reagent [cf. R. Buijle and H. G. Viehe, Angew. Chem. International Edition 3, 582, (1964)] or of an isoxasolium salt reagent [cf. R. B. Woodward, R. A. Olofson and H. Mayer, J. Amer. Chem. Soc. 83, 1010 (1961)], or of a ketenimine reagent [cf. C. L. Stevens and M. F. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., J. Amer. Chem. Soc., 94(11), 4035-4037 (1972) and by T. Nara et al., J. Antibiotics (Japan) 24(5), 321-323 (1971) and in U.S. Pat. No. 3,682,777.

For the coupling of the organic carboxylic acid, including but not limited to a substituted or unsubstituted D-mandelic acid (with or without a protecting group on the α-hydroxyl), as described above with compound II (or a salt or preferably an easily hydrolyzed ester of Schiff base, as with benzaldehyde, thereof) it is also convenient and efficient to utilize as the coupling agent phosphonitrilic chloride trimer (J. Org. Chem., 33(7), 2979-81, 1968) or N-ethoxy-1,2-dihydroquinoline (EEDQ) as described in J. Amer. Chem. Soc., 90, 823-824 and 1652-1653 (1968) and U.S. Pat. No. 3,455,929. The reaction is preferably carried out at 30°-35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a 7-acylaminocephalosporanic acid (prepared by substituting 7-aminocephalosporanic acid for the 3-thiolated-7-aminocephalosporanic acids in the acylation procedures described herein and elsewhere reported) with a thiol having the formula

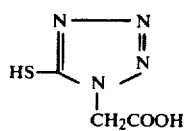

and then removing the protecting group if any is present, as on an α-hydroxy or on the carboxyl group or both. The displacement of such a 3-acetoxy group with such a thiol may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. To provide some specific examples for purposes of illustration but not of limitation, substituted or unsubstituted D-mandelamido-cephalosporanic acids are prepared by the procedures described generally or specifically in J. Med. Chem. 17(1), 34-41 (1974) and the references cited therein. As noted above, the preparation of many other 7-acylamidocephalosporanic acids is described in the patent and scientific literature, e.g. in U.S. Class 260-243C.

When the organic carboxylic acid contains a functional group such as hydroxyl it is often desirable to first block (or protect) the hydroxy group, then carry out the coupling reaction and finally subject the resulting compound to chemical removal of the protecting group, that is, subjecting the resulting compound to elimination reaction of the protecting group.

The term "(lower)alkyl" as used herein means both straight and branched chain aliphatic hydrocarbon radicals having from one to ten carbon atoms such as methyl, ethyl, propyl, isopropol, butyl, isobutyl, t-butyl, amyl, hexyl, 2-ethylhexyl, heptyl, decyl, etc. Similarly, where the term "(lower)" is used as part of the description of another group, e.g. "(lower)alkoxy", it refers to the alkyl portion of such group which is therefore as described above in connection with "(lower)alkyl".

The present invention thus also provides the process for the production of the antibacterial agents having the structure

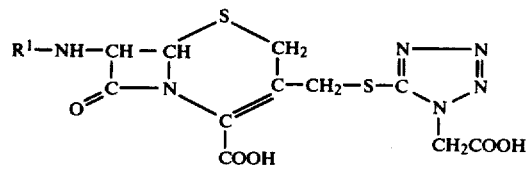

wherein $R^1$ is acyl as defined above which comprises reacting a compound having the formula

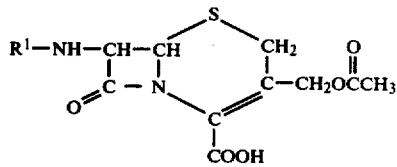

wherein $R^1$ is acyl as defined above with a compound having the formula

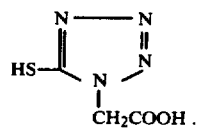

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group.

As indicated above, these five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767–773 (1971). In another good method the triethylamine salt of 7-aminocephalosporanic acid is reacted directly with the active halogen compound, as in United Kingdom Pat. No. 1,229,453.

These esters of 7-aminocephalosporanic acid are then acted with the nucleophile $HSR^2$ in the same manner as is illustrated herein for 7-aminocephalosporanic acid itself. The 3-thiolated ester of 7-aminocephalosporanic acid is then coupled with the organic carboxylic acid as before. Before or after removal of any blocking group, e.g. on the hydroxy group in the 7-sidechain, the ester of the cephalosporin so obtained is, if not used per se, converted to its free acid, including its zwitterion (and, if desired, any salt) by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006–2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

In the treatment of bacterial infections in man, the compounds of this invention are administered parenterally in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excepients. The dosage units are in the form of liquid preparations such as solutions or suspensions.

STARTING MATERIALS

A. 1-Carboxymethyl-5-mercaptotetrazole

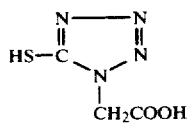

(a) Recrystallization of 1-methyl-5-mercaptotetrazole

Procedure:

1. One hundred and ten grams of 1-methyl-5-mercaptotetrazole is slurried in 350 ml. of boiling chloroform. A near solution is obtained.

2. The hot solution (50°–60°) is rapidly filtered by vacuum through a heated Buchner funnel (11 cm. SS No. 604 paper containing ¼ to ½ inch of packed filter aid ("Supercel"). The filter pad is washed with 50 ml. of 50°–60° C. chloroform which is added to the filtrate.

3. The filtrate is cooled to approximately 0°–6° C. and kept at 0°–6° C. for 2 hours. The crystals which have formed are collected by filtration at 0°–6° C. and washed with 60 ml. of 0°–6° C. chloroform which is added to the filtrate. The crystals (cut A) are air dried at 37°–45° C. for 18 hours.

4. The filtrate is concentrated on the rotary vacuum evaporator (60° C. bath) to approximately one-half volume. This slurry is cooled to 0°–6° C. and kept at 0°–6° C. for 2 hours. The crystals are collected by filtration at 0°–6° C., washed with 40 ml. of 0°–6° C. chloroform which is added to the filtrate. The crystals (cut B) are air dried at 37°–45° C. for 18 hours. Crystal cuts A and B are composited to give an approximate 65% weight yield.

5. The filtrate of cut B, Step 4 may be reworked twice as described in Step 4 to obtain an additional 15% recovery.

(b) Preparation of the Di-sodium Salt of 1-carboxymethyl-5-mercaptotetrazole

Procedure:

1. Five hundred ml. of substantially dry and pure tetrahydrofuran in a 2-liter 3 neck flask with stirrer is cooled in a salt-acetone-ice bath to approximately −10° C. Dry nitrogen gas is blown on the liquid surface.

2. Five hundred ml. of 15.06% (1.6 N) butyl lithium in hexane (Foote Mineral Co.) is added over a ten minute period under dry nitrogen and stirring to the tetrahydrofuran. The near solution is cooled to −5° to −10° C.

3. Forty six and four tenths gram (46.4 g.) of 1-methyl-5-mercaptotetrazole (recrystallized as above) is dissolved in 200 ml. of substantially pure and dry tetrahydrofuran. The solution is filtered if cloudy and then cooled to 5° to 10° C.

4. The cooled solution of step 3 is added over 10 minutes with stirring and under dry nitrogen to the butyl lithium solution. The temperature should be maintained at −5° C. to +10° C. maximum. Precipitates may form.

5. The mixture is stirred under dry nitrogen and 0° C. to +10° C. for one half hour.

6. Anhydrous carbon dioxide gas is bubbled through at a rapid rate and with rapid stirring for 15–30 minutes at approximately ambient temperature (0° to 10° C.) to no higher than +20° C.

7. The white precipitate which forms is suitably collected by filtration in an area of low humidity. The precipitate is washed with about 75 ml. of tetrahydrofuran.

8. The precipitate is dissolved in 250 ml. of water (pH 8.5–9.5). A second layer of tetrahydrofuran may be present. This may be removed in the vacuum rotary evaporator (50° C. bath).

9. The aqueous solution is adjusted to pH 1.6–2.0 with concentrated hydrochloric acid.

10. The acid aqueous solution is extracted twice with 250 ml. portions of ethyl acetate. Each 250 ml. ethyl acetate extract is back extracted with 100 ml. portions of water. The water extracts are discarded. The ethyl acetate extracts (free of any water layer) are filtered and composited.

11. The combined ethyl acetate extracts are concentrated to dryness on the vacuum rotary evaporator (60° C. bath).

12. The crystals in the flask are boiled with 300 ml. of chloroform for about 2 minutes. The hot slurry (50°–60° C.) is vacuum filtered through a heated Buchner funnel (11 cm-SS-604 paper). The crystals are washed with about 75 ml. of 50° C. chloroform. The crystals are air dried at room temperature for about 3 hours and then made about 100–200 mesh.

13. The 100–200 mesh crystals are treated with boiling chloroform exactly as described in step 12 (the hot chloroform removes most of the unreacted 1-methyl-5-mercaptotetrazole). Yield: approximately 45 to 50 grams of crystalline 1-carboxymethyl-5-mercaptotetrazole. These crystals may contain 0.02 to 0.05 moles of 1-methyl-5-mercaptotetrazole.

14. The crystals of step 13 are slurried with 250 ml. of ethyl ether at room temperature for 3-5 minutes. The mixture is filtered. The insolubles (0.5-5%) may be a contaminating symmetrical mercaptotetrazole ketone of the following tentative structure:

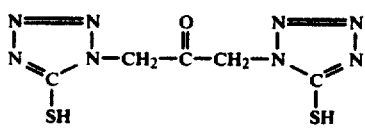

CAUTION: This compound EXPLODES at approximately 205°-210° C.

15. The ether filtrate of step 14 is evaporated to dryness on the vacuum rotary evaporator (50° C. bath). Approximately 42 to 48 grams of crystalline 1-carboxymethyl-5-mercaptotetrazole containing approximately 0.01-0.05 mole of 1-methyl-5-mercaptotetrazole is recovered.

16. The crystals are dissolved in 420 ml. of absolute ethanol (approximately 100 mg./ml.). The solution is warmed to 50°-60° C.

17. To the hot solution of step 16, 310 ml. of a 41% sodium 2-ethylhexanoate (SEH) solution in isopropanol is added with very rapid stirring over a 10 minute period. A crystalline precipitate forms. The mixture is slurried at 50°-60° C. for 20 minutes.

18. The mixture is filtered hot (50°-60° C.) through a heated Buchner funnel (11 cm-SS-No. 604 paper). The crystals are washed with 75 ml. of 50° C. ethanol.

19. The ethanol damp crystals of step 18 are slurried in 200-300 ml. of ethanol. The slurry is passed through a 200 mesh screen. The slurry is heated to 50°-60° C. for 5 minutes with rapid stirring (unreacted di-sodium 1-methyl-5-mercaptotetrazole is very soluble in hot ethanol).

20. The crystals are collected at 50°-60° C. on a 11 cm-SS No. 604 paper in a heated Buchner funnel. The crystals are washed with 75-100 ml. of ethanol and vacuum dried at 50°-60° C. for 24-48 hours. Yield: 40-48 grams of di-sodium 1-carboxymethyl-5-mercaptotetrazole (free of 1-methyl-5-mercaptotetrazole as observed by NMR).

B.
7-Amino-3-(1-carboxymethyltetrazol-5-yl-thiomethyl)-3-cephem-4-carboxylic acid

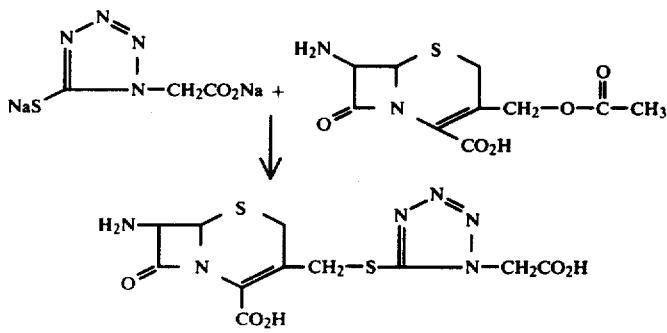

1. Into a 3 necked flask set up with an agitator, a temperature regulator, thermometer and a nitrogen inlet tube, place 18 grams (0.066 mole) of 7-aminocephalosporanic acid, (which has preferably been recrystallized by the toluenesulfonic acid procedure) and 300 ml. of 0.1 M pH 6.4 phosphate buffer (20.7 grams of sodium phosphate, monobasic $0.1H_2O$ + 8.5 grams of sodium phosphate, dibasic, anhydrous, q.s. to 2 liters).

2. With agitation of the mixture described in step 1, add 1.5 grams of sodium bisulfite and 16 grams (0.078 moles) of 1-carboxymethyl-5-mercaptotetrazole disodium.

3. With agitation continuing, bubble nitrogen through the mixture for 10 minutes.

4. Maintaining agitation and nitrogen inflow, heat the slurry over a 20 minute period to 56° C. During this time interval, 6.5 grams of sodium bicarbonate is added in small increments.

5. With continued agitation and nitrogen inflow, maintain the temperature of the solution at 56° C. for 4 hours. The pH should remain at between 6.2-6.6.

6. Cool the reaction mixture in an ice bath to 5° C.

7. Add 50 ml. of a 1:1 phosphoric acid/water solution to the mixture or concentrated HCl to a pH of 2.0-3.0.

8. Collect the product by filtration. Wash the filter cake with 20 ml. of cold water followed by 200 ml. of cold methanol.

9. Air dry the solid to constant weight. (A typical run produced 14.5 grams of product.) This product may vary in color from yellow to dark brown.

10. Pass the product through a 200 mesh stainless steel screen.

11. Suspend 10 grams of the 200 mesh powder in 200 ml. of n-propanol with rapid stirring.

12. Add 2.0 ml. of concentrated hydrochloric acid and stir vigorously for 0.5 hour at room temperature.

13. Filter the slurry. Wash the brown solids with 20 ml. of n-propanol and add the wash to the filtrate (save the filter cake for possible recovery of additional product).

14. Add 1.5 grams of charcoal ("Darco G-60") to the n-propanol filtrate of step 13. Slurry for 0.5 hour. Remove the carbon by filtration. Wash the carbon with 20 ml. of n-propanol and add the wash to the filtrate.

15. With rapid stirring, add triethylamine to the n-propanol filtrate to an apparent pH of 3.0. Crystals form. Slurry for 10 minutes.

16. Collect the white crystals by filtration and wash with 30 ml. of n-propanol, 50 ml. of methanol, and vacuum dry at 40° C. for 24 hours. Yield: 4 to 8 grams of 7-amino-3-(1-carboxymethyltetrazol-5-ylthiomethyl)-3-cephem-4-carboxylic acid.

17. An alternate procedure for the purification of 7-amino-3-(1-carboxylmethyltetrazol-5-ylthiomethyl)-3-cephem-4-carboxylic acid follows:

(a) Slurry 10 grams of the 200 mesh product (from step 10) in 75 ml. of 1 N hydrochloric acid for 10–15 minutes at room temperature. Filter to remove dark brown solids.

(b) Add 2.5 grams of charcoal ("Darco G-60") and slurry for 0.5 hour.

(c) Remove the carbon by filtration. Wash the carbon with 15 ml. of water and add the wash to the filtrate.

(d) With rapid stirring, add concentrated ammonium hydroxide to the filtrate to pH 2.5–3.0. Crystals form.

(e) Slurry the crystal mass for 25 minutes. Remove the crystals by filtration. Wash the crystals with 30 ml. of water, 50 ml. of methanol, and vacuum dry at room temperature. Yield: 4–7 grams of near white crystals.

The other reagents used to prepare the compounds of the present invention are synthesized either as described in the art (e.g. as in the patents and publications noted above) or by strictly analogous procedures. For convenience and purposes of illustration, however, there are given below some specific examples of such syntheses.

Preparation of D-mandelic acid carboxyanhydride

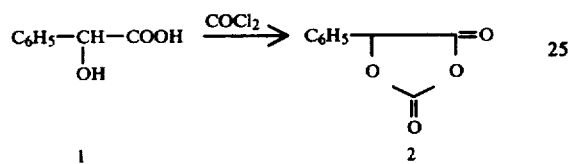

1

D-Mandelic acid carboxyanhydride (2)

Phosgene was bubbled through a solution of 2.0 g. (0.013 mole) of D(−)-mandelic acid (1) in dry tetrahydrofuran for 30 minutes. The solution was allowed to stand overnight after which time it was heated under reflux for 10 minutes. Evaporation of the solvent under reduced pressure afforded an oily residue which was solidified by trituration with n-hexane (20 ml.). The product was collected by filtration and dried in vacuo on KOH. Yield 2.3 g. of D-mandelic acid carboxyanhydride.

IR: $v_{max}^{nuj}$ 1895, 1875, 1780 cm$^{-1}$.

buffer pH 6.4 to which is added 0.31 mole disodium 1-carboxymethyl-5-mercaptotetrazole. The solution is heated at 55° C. under a nitrogen atmosphere for 5 hr. After 1 hr. the pH is adjusted to 6.4 by addition of a small amount of 40% H$_3$PO$_4$. At the end of the 5 hr. heating period, the solution is cooled to 23° C. and the pH adjusted to 2 by addition of 3 N HCl under a layer of ethyl acetate. The product is extracted into ethyl acetate and stirred for 15 min. at 23° C. with 2 g. of ("Darco KB") decolorizing charcoal. It is then filtered through a pad of diatomaceous earth ("Celite") and the ethyl acetate removed under vacuum to leave an oil which is triturated to a solid with diethyl ether, collected by filtration and dried over P$_2$O$_5$ under vacuum to yield solid 7-phenoxyacetamido-3-(1-carboxymethyl-tetrazol-5-ylthiomethyl)-3-cephem-4-carboxylic acid.

The following examples are given in illustration of, but not in limitation of, the present invention. All temperatures are in degrees Centigrade. 7-Aminocephalosporanic acid is abbreviated as 7-ACA; -ACA-represents the moiety having the structure

and thus 7-ACA can be represented as

H—ACA—O—$\overset{\overset{O}{\|}}{C}$—CH$_3$.

DESCRIPTION OF THE PREFERRED EMBODIMENTS

EXAMPLE 1

Dipotassium 7-(D-α-hydroxyphenylacetamido)-3-(1-carboxymethyl-tetrazol-5-ylthiomethyl)-3-cephem-4-carboxylate

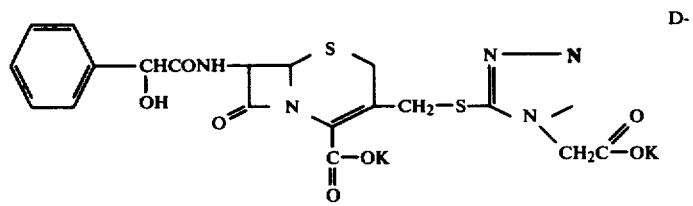

Among the most active compounds of the present invention are those having the D configuration at the α-carbon atom in the 7-side chain, that is, those made from D-mandelic acid or a monosubstituted D-mandelic acid as illustrated herein. In addition, the configuration at the two optically active, asymmetric centers in the β-lactam nucleus is that found in cephalosporin C produced by fermentation and in the 7-aminocephalosporanic acid derived therefrom.

7-Phenoxyacetamido-3-(1-carboxymethyltetrazol-5-ylthiomethyl)-3-cephem-4-carboxylic acid by thiolation of 7-phenoxyacetamidocephalosporanic acid Sodium 7-phenoxyacetamidocephalosporanate (0.27 mole) is suspended in 1000 ml. of 0.1 M phosphate To a suspension of 500 mg. (0.0134 mole) of 7-amino-3-(1-carboxymethyltetrazol-5-ylthiomethyl)-3-cephem-4-carboxylic acid in 10 ml. of water at 0° was added with stirring 200 mg. of sodium bicarbonate. As soon as the solution was complete 340 mg. (0.172 mole) of D-(−)-2-formyloxy-2-phenylacetyl chloride was added all at once in 10 ml. of acetone. As soon as a precipitate formed, solid sodium bicarbonate was added and the solution was stirred at pH 8 for 1 hr. The acetone was evaporated at 15 mm at 30°, and the solution was layered with 20 ml. of ethyl acetate and acidified with 1:1 phosphoric acid. After extraction with ethyl acetate, the mixture was filtered and the organic layer was separated. The ethyl acetate was evaporated to a solid which was dissolved in 5 ml. of methanol and 5 drops of conc. hydrochloric acid. The solution was treated with carbon and heated for 3 min. on the steambath. The mixture was filtered and diluted with 15 ml. of water. The gummy solid was triturated with cold water and finally with anhydrous ether. The solid was dissolved in 5 ml. of acetone and was treated with 50 mg. of potassium 2-ethylhexanoate. Dipotassium 7-(D-α-hydroxyphenylacetamido)-3-(1-carboxymethyltetrazol-5-ylthiomethyl)-3-cephem-4-carboxylate, as a white solid, was collected and weighed 90 mg. m.p. 175° slow decomp.

Anal. Calcd. for $C_{19}H_{16}K_2N_6O_7S_2$: C, 39.19; H, 2.77; N, 14.42. Found: C, 39.87; H, 3.50; N, 12.58.

EXAMPLE 2

Substitution in the procedure of Example 1 of an equimolar weight of the carboxyanhydrides prepared from the monosubstituted D-mandelic acids
D-2-chloro-mandelic acid,
D-3-chloro-mandelic acid,
D-4-chloro-mandelic acid,
D-2-bromo-mandelic acid,
D-3-bromo-mandelic acid,
D-4-bromo-mandelic acid,
D-2-fluoro-mandelic acid,
D-3-fluoro-mandelic acid,
D-4-fluoro-mandelic acid,
D-2-trifluoromethyl-mandelic acid,
D-3-trifluoromethyl-mandelic acid,
D-4-trifluoromethyl-mandelic acid,
D-2-amino-mandelic acid,
D-3-amino-mandelic acid,
D-4-amino-mandelic acid,
D-2-nitro-mandelic acid,
D-3-nitro-mandelic acid,
D-4-nitro-mandelic acid,
D-2-hydroxy-mandelic acid,
D-3-hydroxy-mandelic acid,
D-4-hydroxy-mandelic acid,
D-2-methyl-mandelic acid,
D-3-methyl-mandelic acid,
D-4-methyl-mandelic acid,
D-2-methoxy-mandelic acid,
D-3-methoxy-mandelic acid,
D-4-methoxy-mandelic acid respectively produces
  Dipotassium 7-(D-2-chloro-mandelamido)-3-(1-carboxymethyltetrazol-5-ylthiomethyl)-3-cephem-4-carboxylate,
  Dipotassium 7-(D-3-chloro-mandelamido)-3-(1-carboxymethyltetrazol-5-ylthiomethyl)-3-cephem-4-carboxylate,
  Dipotassium 7-(D-4-chloro-mandelamido)-3-(1-carboxymethyltetrazol-5-ylthiomethyl)-3-cephem-4-carboxylate,
  Dipotassium 7-(D-2-bromo-mandelamido)-3-(1-carboxymethyltetrazol-5-ylthiomethyl)-3-cephem-4-carboxylate,
  Dipotassium 7-(D-3-bromo-mandelamido)-3-(1-carboxymethyltetrazol-5-ylthiomethyl)-3-cephem-4-carboxylate,
  Dipotassium 7-(D-4-bromo-mandelamido)-3-(1-carboxymethyltetrazol-5-ylthiomethyl)-3-cephem-4-carboxylate,
  Dipotassium 7-(D-2-fluoro-mandelamido)-3-(1-carboxymethyltetrazol-5-ylthiomethyl)-3-cephem-4-carboxylate,
  Dipotassium 7-(D-3-fluoro-mandelamido)-3-(1-carboxymethyltetrazol-5-ylthiomethyl)-3-cephem-4-carboxylate,
  Dipotassium 7-(D-4-fluoro-mandelamido)-3-(1-carboxymethyltetrazol-5-ylthiomethyl)-3-cephem-4-carboxylate,
  Dipotassium 7-(D-2-trifluoromethyl-mandelamido)-3-(1-carboxymethyltetrazol-5-ylthiomethyl)-3-cephem-4-carboxylate,
  Dipotassium 7-(D-3-trifluoromethyl-mandelamido)-3-(1-carboxymethyltetrazol-5-ylthiomethyl)-3-cephem-4-carboxylate,
  Dipotassium 7-(D-4-trifluoromethyl-mandelamido)-3-(1-carboxymethyltetrazol-5-ylthiomethyl)-3-cephem-4-carboxylate,
  Dipotassium 7-(D-2-amino-mandelamido)-3-(1-carboxymethyltetrazol-5-ylthiomethyl)-3-cephem-4-carboxylate,
  Dipotassium 7-(D-3-amino-mandelamido)-3-(1-carboxymethyltetrazol-5-ylthiomethyl)-3-cephem-4-carboxylate,
  Dipotassium 7-(D-4-amino-mandelamido)-3-(1-carboxymethyltetrazol-5-ylthiomethyl)-3-cephem-4-carboxylate,
  Dipotassium 7-(D-2-nitro-mandelamido)-3-(1-carboxymethyltetrazol-5-ylthiomethyl)-3-cephem-4-carboxylate,
  Dipotassium 7-(D-3-nitro-mandelamido)-3-(1-carboxymethyltetrazol-5-ylthiomethyl)-3-cephem-4-carboxylate,
  Dipotassium 7-(D-4-nitro-mandelamido)-3-(1-carboxymethyltetrazol-5-ylthiomethyl)-3-cephem-4-carboxylate,
  Dipotassium 7-(D-2-hydroxy-mandelamido)-3-(1-carboxymethyltetrazol-5-ylthiomethyl)-3-cephem-4-carboxylate,
  Dipotassium 7-(D-3-hydroxy-mandelamido)-3-(1-carboxymethyltetrazol-5-ylthiomethyl)-3-cephem-4-carboxylate,
  Dipotassium 7-(D-4-hydroxy-mandelamido)-3-(1-carboxymethyltetrazol-5-ylthiomethyl)-3-cephem-4-carboxylate,
  Dipotassium 7-(D-2-methyl-mandelamido)-3-(1-carboxymethyltetrazol-5-ylthiomethyl)-3-cephem-4-carboxylate,
  Dipotassium 7-(D-3-methyl-mandelamido)-3-(1-carboxymethyltetrazol-5-ylthiomethyl)-3-cephem-4-carboxylate,
  Dipotassium 7-(D-4-methyl-mandelamido)-3-(1-carboxymethyltetrazol-5-ylthiomethyl)-3-cephem-4-carboxylate,
  Dipotassium 7-(D-2-methoxy-mandelamido)-3-(1-carboxymethyltetrazol-5-ylthiomethyl)-3-cephem-4-carboxylate,
  Dipotassium 7-(D-3-methoxy-mandelamido)-3-(1-carboxymethyltetrazol-5-ylthiomethyl)-3-cephem-4-carboxylate and
  Dipotassium 7-(D-4-methoxy-mandelamido)-3-(1-carboxymethyltetrazol-5-ylthiomethyl)-3-cephem-4-carboxylate respectively.

EXAMPLE 3

Substitution for the D-mandelic acid carboxyanhydride in the procedure of Example 2 of an equimolar weight of the carboxyanhydride prepared in similar fashion from D-2-thiopheneglycolic acid and D-3-thiopheneglycolic acid respectively produces dipotassium 7-(D-α-hydroxy-2-thienylacetamido)-3-(1-carboxymethyltetrazol-5-ylthiomethyl)-3-cephem-4-carboxylate and dipotassium 7-(D-α-hydroxy-3-thienylacetamido)-

3-(1-carboxymethyltetrazol-5-yl-thiomethyl)-3-cephem-4-carboxylate respectively.

Samples of the compound prepared in Example 1 after solution in water and dilution with Nutrient Broth were found to exhibit the following Minimum Inhibitory Concentrations (M.I.C.) in mcg./ml. versus the indicated micro-organisms as determined by overnight incubation at 37° C. by Tube Dilution.

| In Vitro Antibacterial Activity M.I.C. (mcg./ml.) | | |
|---|---|---|
| Organisms | | Ex. 1 |
| Str. pneumoniae* $(10^{-3})$** | A9585 | 0.6 |
| Str. pyrogenes* $(10^{-3})$ | A9604 | 0.6 |
| S. aureus Smith $(10^{-4})$ | A9537 | 1.3 |
| S. aureus-50% serum $(10^{-4})$ | A9537 | 16 |
| S. aureus BX1633 $(10^{-3})$ | A9606 | 2.5 |
| S. aureus BX1633 $(10^{-2})$ | A9606 | 4 |
| S. aureus Meth-Res $(10^{-3})$ | A15097 | 8 |
| Sal. enteritidis $(10^{-4})$ | A9531 | 0.08 |
| E. coli Juhl $(10^{-4})$ | A15119 | 4 |
| E. coli $(10^{-4})$ | A9675 | 32 |
| K. pneumoniae $(10^{-4})$ | A9977 | 1 |
| K. pneumoniae $(10^{-4})$ | A15130 | 32 |
| Pr. mirabilis $(10^{-4})$ | A9900 | 0.5 |
| Pr. morganii $(10^{-4})$ | A15153 | 16 |
| Ps. aeruginosa $(10^{-4})$ | A9843A | >125 |
| Ser. mercescens $(10^{-4})$ | A20019 | >125 |
| Ent. cloacae $(10^{-4})$ | A9656 | >125 |
| Ent. cloacae $(10^{-4})$ | A9657 | 2 |
| Ent. cloacae $(10^{-4})$ | A9659 | >125 |

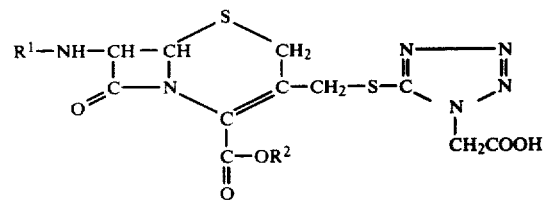

*45% Antibiotic Assay Broth + 50% Nutrient Broth + 5% serum
**Dilution of overnight broth culture

We claim:
1. A compound of the formula

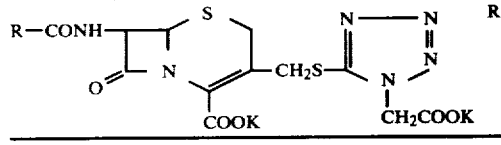

wherein $R^2$ is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl and having the D configuration in the 7-side chain wherein $R^1$ has the structure

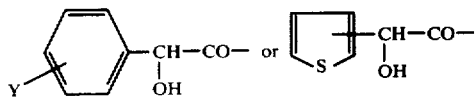

and Y is hydrogen, chlorine, bromine, fluorine, trifluoromethyl, amino, nitro, hydroxy, lower alkyl of 1-4 carbon atoms or lower alkoxy of 1-4 carbon atoms.

2. A nontoxic pharmaceutically acceptable salt of a compound of claim 1.

3. A compound of claim 1 wherein $R^2$ is hydrogen.

4. A nontoxic pharmaceutically acceptable salt of a compound of claim 3.

5. The compound of claim 1 having the D configuration in the 7-side chain wherein $R^1$ has the structure

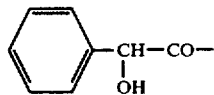

and $R^2$ is hydrogen.

6. A nontoxic pharmaceutically acceptable salt of the compound of claim 5.

7. The compound of claim 1 having the D configuration in the 7-side chain wherein $R^1$ has the structure

and $R^2$ is hydrogen.

8. A nontoxic pharmaceutically acceptable salt of the compound of claim 7.

9. The compound of claim 1 having the D configuration in the 7-side chain wherein $R^1$ has the structure

and $R^2$ is hydrogen.

10. A nontoxic pharmaceutically acceptable salt of a compound of claim 9.

11. A compound having the formula

13. A compound of the formula:

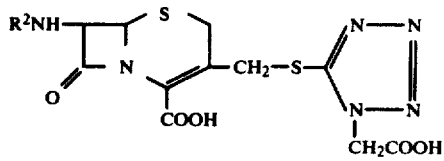

wherein $R^2$ has the structure

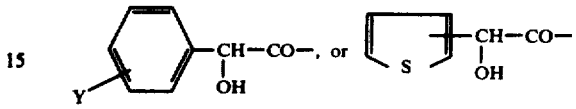

and Y is hydrogen or hydroxy and sodium and potassium salts thereof.

14. A compound of the formula

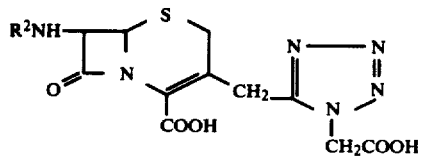

wherein $R^2$ is

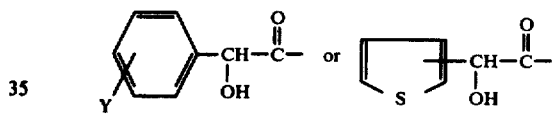

and Y is hydrogen or hydroxy, or a non-toxic pharmaceutically acceptable salt thereof.

* * * * *

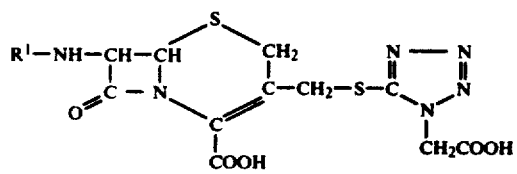

wherein $R^1$ has the formula

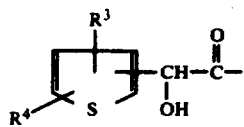

wherein $R^3$ and $R^4$ are each hydrogen, chloro, bromo, fluoro, iodo, nitro, (lower)alkyl, (lower)alkoxy, (lower)alkylthio, di(lower)alkylamino, (lower)alkanoylamino, (lower)alkanoyl or (lower)alkylsulfonyl.

12. A compound of the formula:

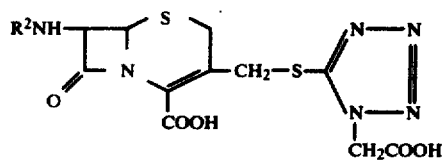

wherein $R^2$ has the structure

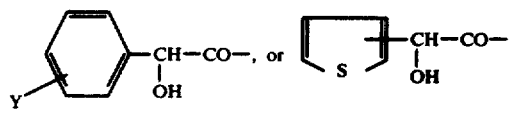

and Y is hydroxy.